United States Patent [19]

Regula et al.

[11] Patent Number: 5,346,501
[45] Date of Patent: Sep. 13, 1994

[54] LAPAROSCOPIC ABSORBABLE ANASTOMOSIC FASTENER AND MEANS FOR APPLYING

[75] Inventors: Donald W. Regula, Belle Meade; Michael F. Bregen, Lebanon, both of N.J.; Zoltan Szabo, San Francisco; Barry N. Gardiner, Orinda, both of Calif.

[73] Assignee: Ethicon, Inc., Somerville, N.J.

[21] Appl. No.: 14,019

[22] Filed: Feb. 5, 1993

[51] Int. Cl.⁵ .............................. A61B 17/00
[52] U.S. Cl. .................. 606/151; 606/153; 606/154; 606/215
[58] Field of Search ........... 606/139, 148, 151, 152, 606/153, 154, 142, 143, 205–208, 213, 215, 216

[56] References Cited

U.S. PATENT DOCUMENTS

| | | | |
|---|---|---|---|
| 3,254,650 | 6/1966 | Collito | 606/153 |
| 4,476,863 | 10/1984 | Kanshin et al. | |
| 4,523,592 | 6/1985 | Daniel | 606/153 |
| 4,598,712 | 7/1986 | Rebuffat et al. | |
| 4,635,638 | 1/1987 | Weintraub et al. | 606/147 |
| 4,667,673 | 5/1987 | Li | 606/153 |
| 4,681,108 | 7/1987 | Rosati et al. | |
| 4,747,407 | 5/1988 | Liu et al. | 606/153 |
| 4,917,114 | 4/1990 | Green et al. | 227/179 |
| 4,957,499 | 9/1990 | Lipatov et al. | 606/153 |
| 5,104,394 | 4/1992 | Knoepfler | 606/143 |
| 5,139,513 | 8/1992 | Segato | 606/219 |
| 5,141,516 | 8/1992 | Detweiler | 606/154 |
| 5,180,392 | 1/1993 | Skeie et al. | 623/11 |
| 5,250,058 | 10/1993 | Miller et al. | 606/153 |

FOREIGN PATENT DOCUMENTS

| | | |
|---|---|---|
| 0070923 | 2/1983 | European Pat. Off. . |
| 0335552 | 10/1989 | European Pat. Off. . |
| 7400096 | 7/1975 | Netherlands ............ 606/153 |

Primary Examiner—Stephen C. Pellegrino
Assistant Examiner—Jeffrey A. Schmidt
Attorney, Agent, or Firm—Paul A. Coletti

[57] ABSTRACT

A mechanism and applier therefor which is capable of inverted anastomosis of two lumens by an absorbable fastener. The fastener is made from two washer-like plate assemblies and a pair of introducers. Each such plate assembly has slots to receive latching prongs protruding from the other plate, and pins to impale tissue. Fastening is done through an applier that causes the pins to pierce the tissue, and causes a knife blade to cut through excess tissue. Fastening is done by attaching fastener halves. Insertion and removal of the fastener and applier optimally is done in an endoscopic procedure through a trocar or through the surgical incision in an open procedure. The system can be used such that the plates can be placed to properly set gaps between and anastomose tissue. The introducer portion will soften intraluminally and be expelled, in about 24 hours. The coupler portion will remain in place for 2–3 weeks, typically, and then fragment and be expelled with the feces.

30 Claims, 6 Drawing Sheets

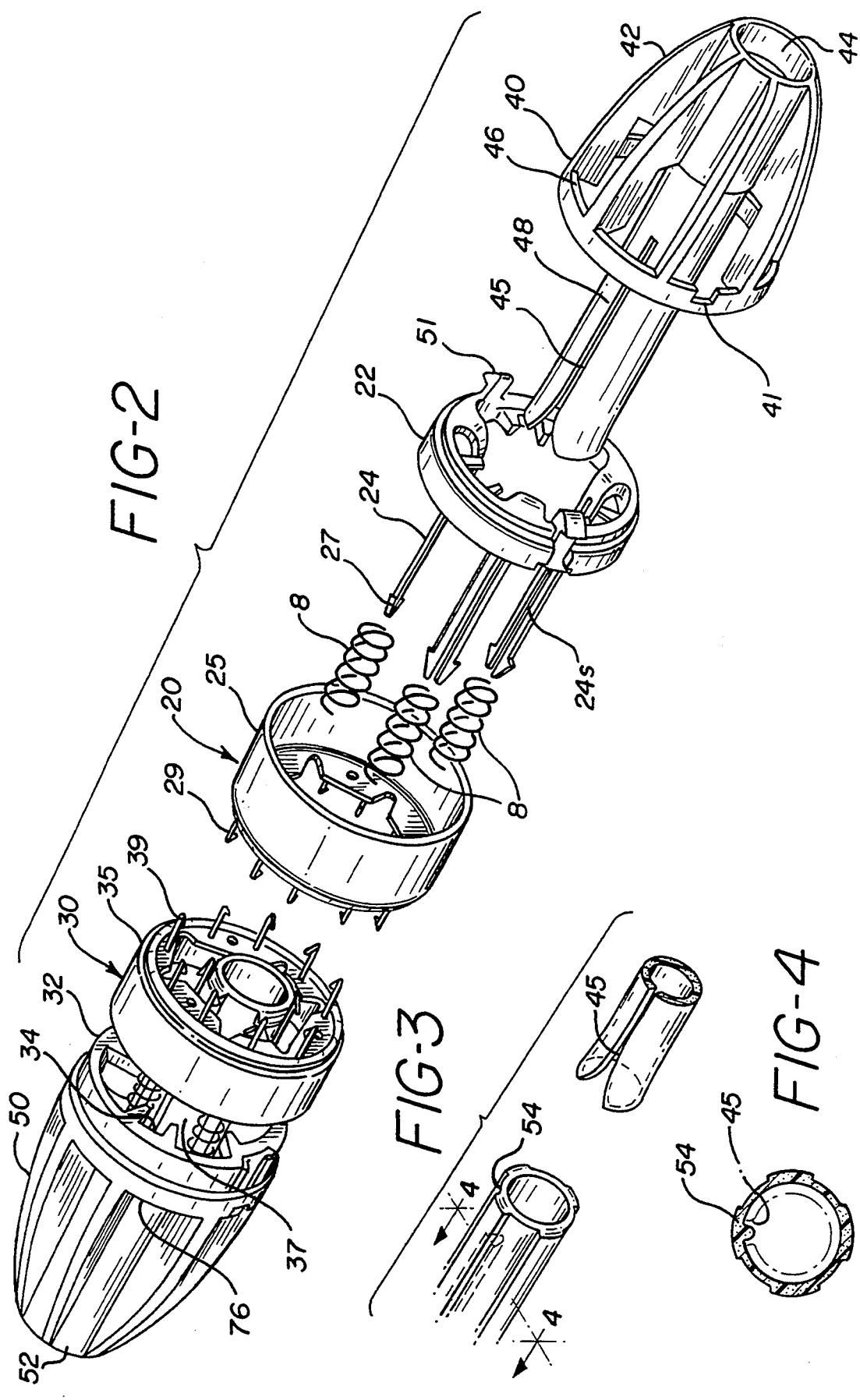

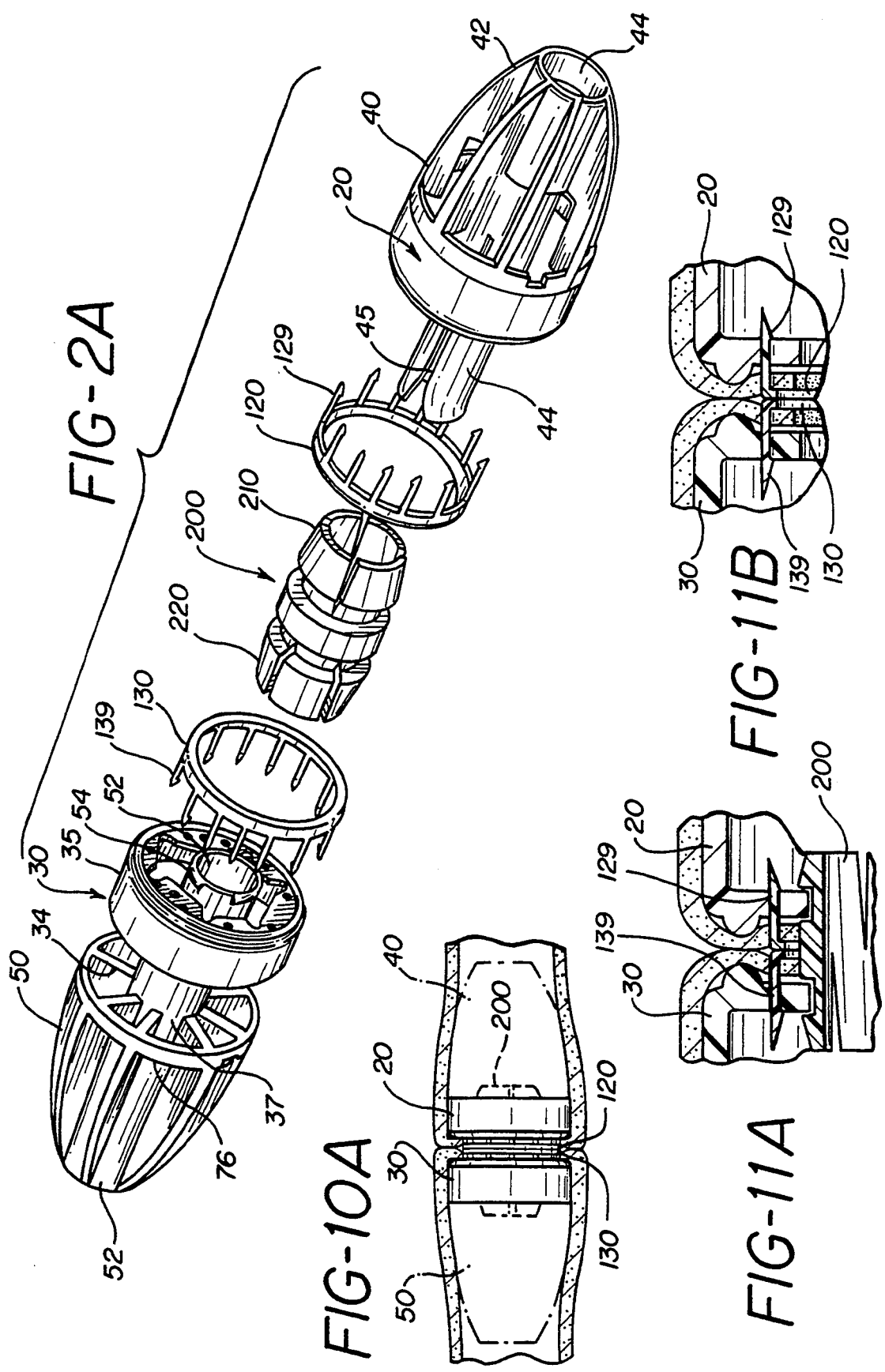

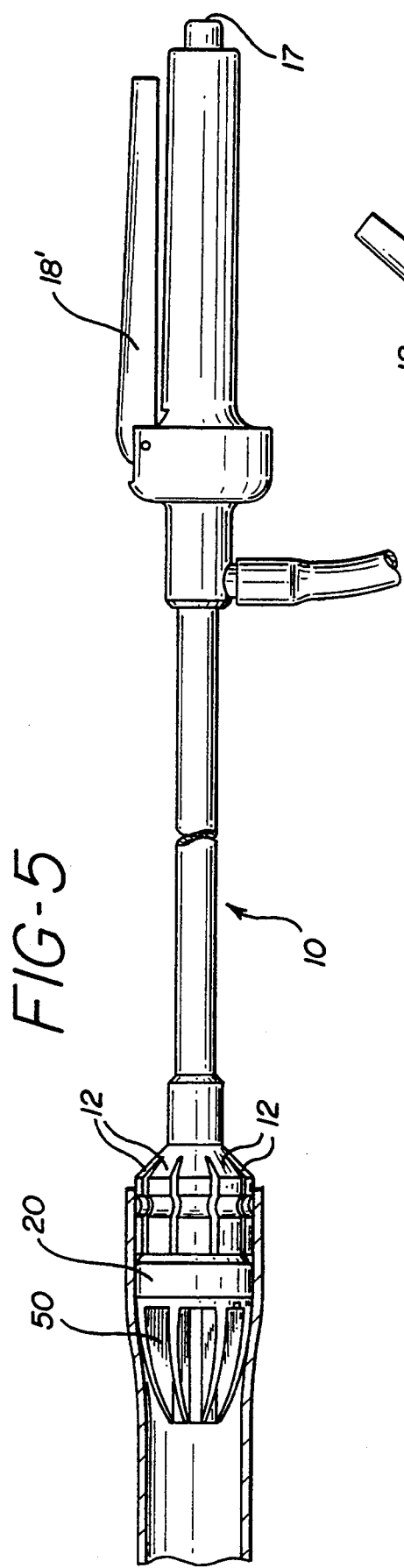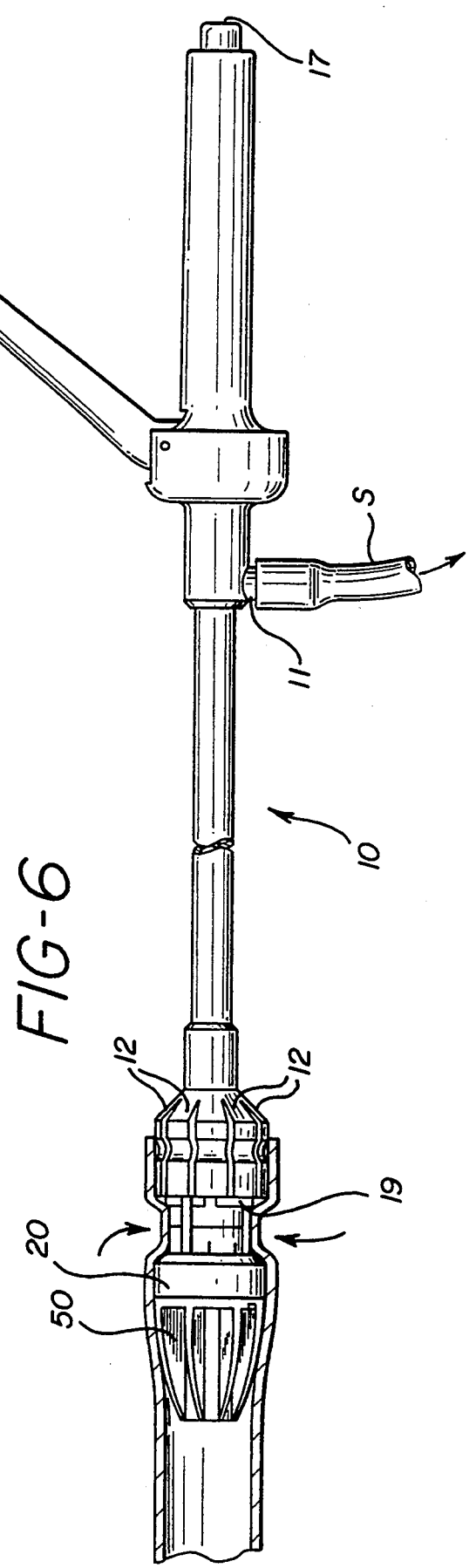

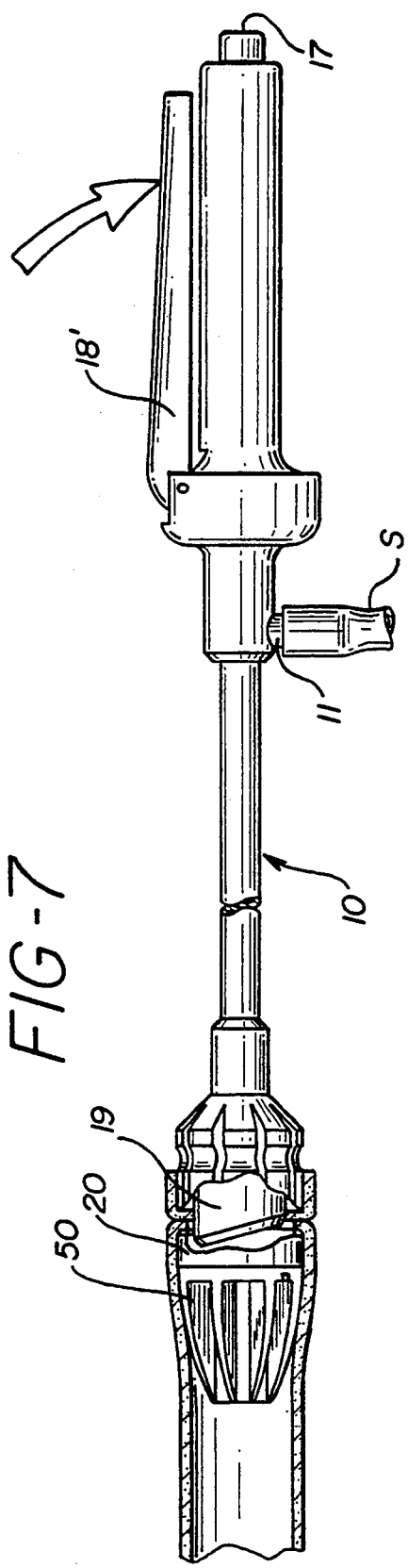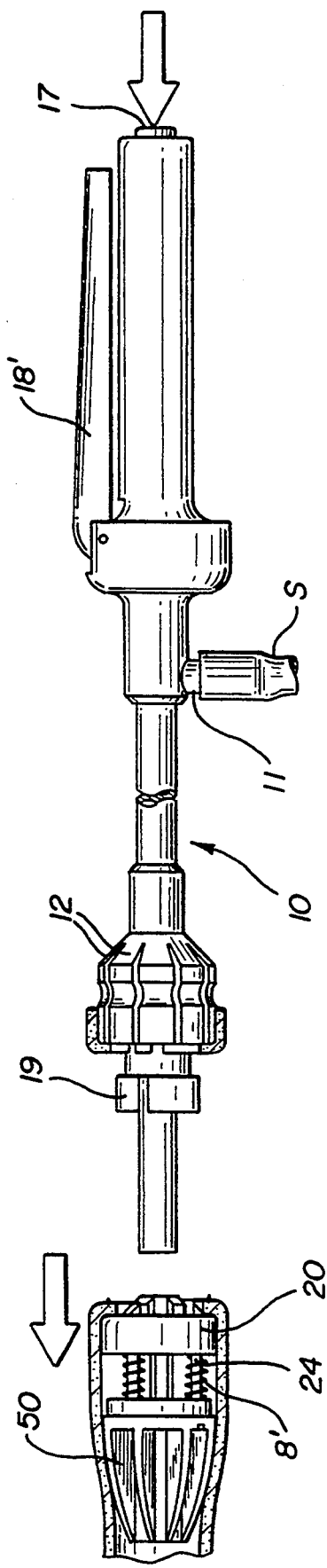

LAPAROSCOPIC ABSORBABLE ANASTOMOSIC FASTENER AND MEANS FOR APPLYING

FIELD OF THE INVENTION

This invention relates to an apparatus for circular anastomotic fastening of tubular organs using absorbable or biodegradable mechanical couplers, and the means to apply such couplers.

BACKGROUND OF THE INVENTION

Currently, there exist a number of surgical anastomotic circular staplers. Generally, these staplers are used to perform an inverted connection of severed tissue with a circular ring of staples displayed around a circumference to connect the tissue. An inverted connection is one where serosa is joined to serosa. In some instances, to maximize the inside diameter of the lumen, a knife mechanism is used to cut the excess tissue within the circumference of the staple ring. The ring of staples is generally a number of small metallic surgical staples, usually between 20 and 40 staples, which form a ring roughly 2 cm to 4 cm in diameter. Naturally, with the inverted connection and with the circular rows of staples there will be some constriction of the tissue during and after healing. Ideally, the lumen diameter at the anastomotic site must be maintained as near as possible to that of the normal healthy bowel, prior to the procedure, to allow normal passage of semisolid materials.

With this type of anastomosis, to prevent infection and abscess, there must be a complete 360° seal of tissue so that no gaps exist between the connected tissue. In addition, it is naturally desirable that when the tissue is connected, the interior volume of the lumen within which the tissue is cut be maintained so that resectioned vessel tissue is continually able to pass fluids while encountering only a minimum of constricting tissue.

In addition, with such circular anastomotic devices it is often desirable to make applier tools which are disposable. That is, disposable instruments are now well accepted by surgeons. Disposable surgical staplers and the like also help prevent the spreading of bacteria or germs. Naturally, the surgeon also desires an instrument which gives good-off-the-shelf reliability and allows a controlled one-handed operation. If necessary to meet the above criteria, it should be possible to construct this device applier to meet disposable needs.

It is also desirable to replace a standard staple line with two adaptively connectable couplers or fasteners. In this way, the need for bending of staples is removed, and yet closure and hemostasis are possible. Of course, by attempting to formulate a system in which a standard staple line is replaced, it would be desirable to formulate such a stapler so that the stapler itself can be pulled through the attached part of the tissue without the need for removing the anvil portion of the stapler. This results in a rapid and efficient method of removing the stapler.

In the desire for creating such a adaptively connectable mating coupler/fastener, it is naturally desirable that these fasteners are both positively aligned and latching, and that they are formulated so that the instrument creates closure with some constantly adjustable closure pressure. If the pressure required to attach the latching members together remains constant, it is much easier to close and latch the instrument with a smooth, efficient single stroke. Alternately, it may be desirable to rely on the constant closure pressure to attach the fastener through the tissue, and then, in a separate action, actually close the tissue with the instrument.

The inventions described in Ser. No. 642,696, entitled "Pull Through Anastomotic Intraluminal Stapler with Absorbable Fastener Means" and U.S. Pat. No. 5,250,058 entitled "Absorbable Anastomotic Fastener Means", assigned to a common assignee, and herein incorporated by reference, provide a mechanism arranged to anastomose two lumens with an absorbable fastener. The fastener is created from two washer-like pieces and is similar to that described above. One of the washer-like pieces has holes which are adaptable to receive latching prongs protruding from the other such washer-like piece. Fastening is accomplished through a singular linear motion in which the prongs pierce the tissue, then latch within the holes in the receiver. Finally, the tissue is cut by a substantially circular knife which also creates a final ring-like shape of the fastener within the tissue. The inner portion of each of the washer-like pieces is removed along with the cut tissue when the instrument is removed from the lumen.

With conventional circular staplers (both metallic and absorbable) it is necessary to perform the resectioning of vessels by first tying the vessel ends individually around a center section of the staple applier. This is necessary to assure that the entire circumference of the open tubular vessel is within the inverted junction. This procedure is commonly called a "purse-string" in that it resembles the tie around the open neck of a purse. It is a difficult and time consuming procedure to do in an open procedure and nearly impossible except for the most adept surgeons, to do laproscopically.

SUMMARY OF THE INVENTION

It is therefore an object of this invention to provide a circular anastomotic device which provides an aligned inverted junction between distal and proximal halves of tubular organs, especially the small and large bowel, without the need for purse string suturing.

It is further an object of the invention to provide an absorbable or otherwise biodegradable circular anastomotic device which provides such alignment, and such an inverted junction for healing.

It is yet another object of the invention to provide a means with which to apply such an absorbable fastener, and yet maintain alignment between fastener halves.

It is further desirable to create a surgical anastomotic device applier which accomplishes these criteria while allowing the user to cut and remove inner portions of tissue that can be considered as excess and which could constrict the volume of material which passes through the connected lumen, without regard to its viscosity.

It is again desirable that the device and applier be shaped to enhance introduction into the lumen of a vessel with a minimum of manipulative activity.

It may yet be more desirable to apply vacuum or suction through the instrument to assist in said manipulation.

It is further desirable that the device be introduced into the lumen in two steps: first, distal or proximal, and then the converse. For example, one half of the device is introduced into the proximal lumen, impaled to the tissue wall and the excess tissue cut. These steps are then repeated for the distal lumen, with the other half.

It is therefore desirable that the actual rejoining of the two vessel halves be accomplished in a third step. This step involves the joining of distal and proximal portions through the use of manual means or manually assisted means.

It is most desirable to provide such an anastomotic coupler and coupler applying mechanism in a device which can be used laparoscopically, for instance in a surgical trocar having a diameter anywhere from about 10 mm to 33 mm.

The anastomotic coupling device disclosed consists of two halves that are joined internal to the body, to resection bowel or other similar tubular vessels. The device is such that this procedure can be accomplished in an open procedure or be used within a laparoscopic procedure. Each half consists of an introducer portion and a staple and compression portion. After healing is attained, expulsion from the body is accomplished in two phases. The introducer part consists of a material that softens or disintegrates in the colon, shortly after the surgical procedure is completed and is expelled in approximately 24 hours to 48 hours. The mechanism of softening or disintegration can be partial dissolution or hydrolyses or chemical, enzymatic reaction. The compression portion is left in place to allow for healing of the joint. The material of this portion remains functional for sufficient time to accomplish healing, typically 2 to 3 weeks, and then fragments or softens to be expelled by the body.

The device is delivered into the abdominal cavity in two or more steps, distal first and then proximal, as an example. One half is loaded onto a cylindrical applier that provides a stable handling platform, as well as a positioning means for inserting into each bowel section. The applier interfaces with the anastomotic coupler by means of a latching mechanism that is operable by actuation of a trigger in the handle. When used in a laparoscopic procedure, this handle remains external to the body cavity through a trocar cannula. The combined device and applier form a generally cylindrical shape. The handle allows the surgeon to position the coupler body half into the colon lumen, with an assistant manipulating the bowel by means of a clamp or other similar manipulators. The applier can be designed to mechanically articulate to further facilitate placement of the bowel without deviation from the intent of this invention.

Once within the distal lumen of the sectioned bowel, for example, the surgeon holds the applier handle while actuating the lever to retract an impaling mechanism. This action will expose the impaling pins located around the radius and within the compression ring. The surgeon will manipulate the tissue wall onto the pins. To assist in the manipulation of the bowel and to secure it to the coupler half, the surgeon may apply suction to a connector on the applier handle. Suction can be transmitted via the hollow shaft of the applier to holes in the body circumference of the introducer.

The surgeon then closes the impaler by actuating its lever, which first, places the tissue wall to be impaled onto the barbed pins. Then, second, the action will engage an essentially cylindrical knife that travels axially toward the coupler half to cut the internal lumen. The next step is to release the bowel and coupler half from the applier, and repeat these steps for the opposite portion of the bowel.

After the proximal and distal sections of the bowel have both been fitted to each half of the coupler, the applier is withdrawn and the surgeon grasps the halves of the coupler/bowel with graspers, or some other surgical specific instrument (or with his fingers if done as an open procedure). The mating portions are placed in close proximity and engage latching portions on either coupler half, snapping two halves together in until the desired compression is achieved at the junction of the lumen.

The desired compression can be accomplished in several ways. As examples this could be by spring loading the latching mechanism in a manner similar to the drawing of FIG. 2, as later described, by use of a compression foam in place of the springs shown in FIG. 2, by use of a ratchet mechanism on the latching arms, or by predetermined fixed gap, selectable by the device or by the surgeon, and based on tissue thickness.

DETAILED DESCRIPTION OF THE DRAWINGS

The invention will be better understood by the attached drawings in which:

FIG. 2 is an exploded perspective view of the coupler as seen in FIG. 1;

FIG. 2A is an exploded perspective view of a coupler as in FIG. 1, with an inverted impaling ring and a separate latching mechanism;

FIG. 3 is a perspective view of the mating portions of the anastomotic attachment coupler as seen in FIG. 2;

FIG. 4 is a cross section of a mating half of FIG. 3, taken across lines 4—4;

FIG. 5, 6, 7 and 8 are plan views of the attachment mechanism of FIG. 1 applying a fastener of FIG. 2;

FIG. 10A is a view similar to FIG. 10 of the coupler configuration of FIG. 2A;

FIGS. 11A and 11B are views of the configuration of FIG. 2A taken in an orientation similar to FIG. 11.

DETAILED DESCRIPTION OF THE INVENTION

Figure 1:
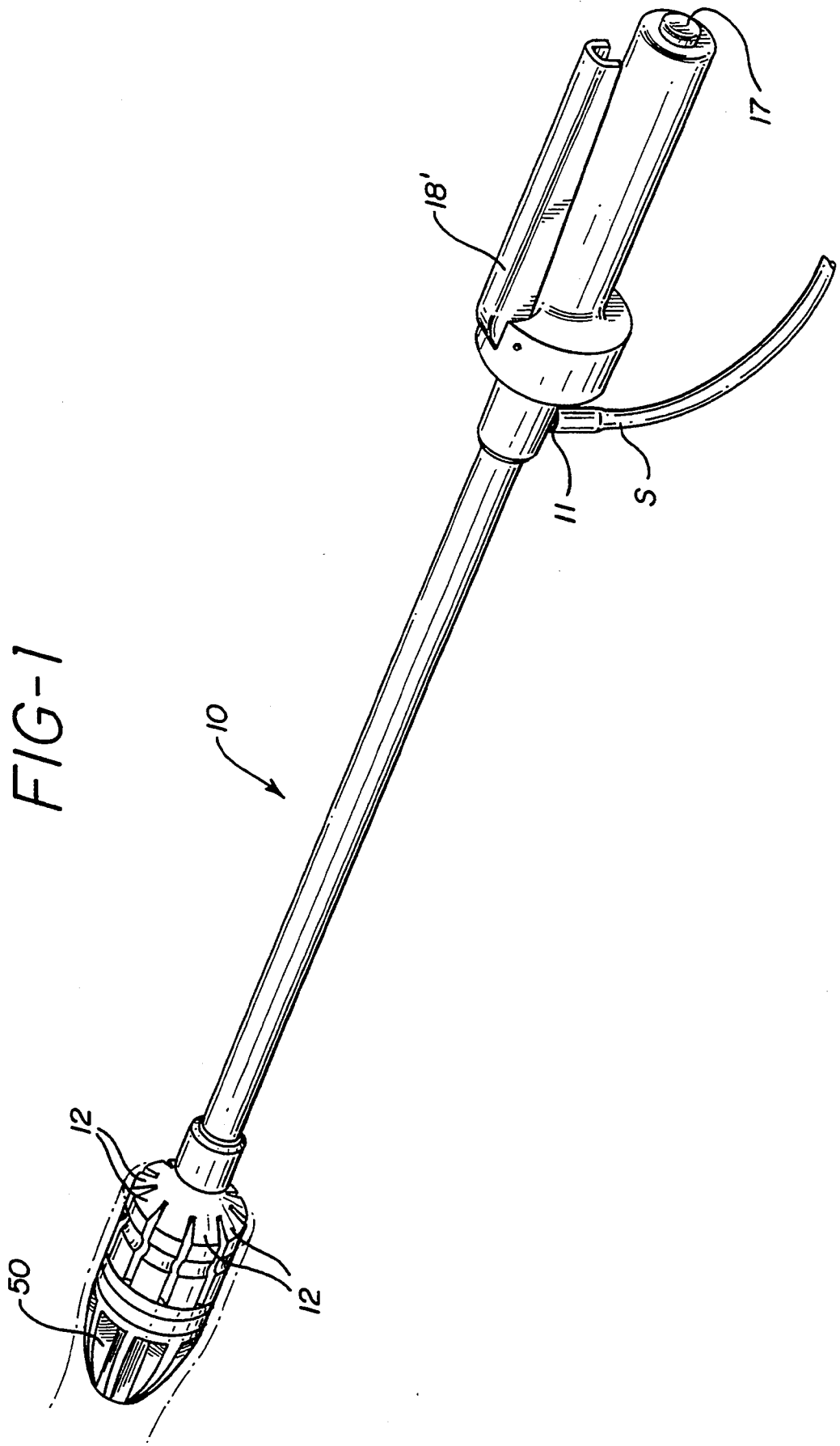
FIG. 1 is a perspective view of an applier of the invention.

There is disclosed in this invention an anastomotic fastener applier 10, useful in combination with introducer means 40,50 and compression means 20,30. Each of these elements is readily apparent when viewing FIGS. 1 through 11, and will be further described herein.

As seen in FIG. 2, there are provided compression members or fasteners 20,30. These fasteners 20, 30 are generally absorbable and are readily formed from known biocompatible materials such as, for example, polydioxanone, polyglycolide, polylactide, copolymers of lactide and glycolide, copolymers of 1,4-dioxanone and lactide or glycolide, copolymers of ε-caprolactone and lactide or glycolide, copolymers of trimethylcarbonate and glycolide, and various other polymers and blends of the aforementioned copolymers and homopolymers. The polymers listed above may also contain a filler such as calcium carbonate, tricalcium phosphate, magnesium oxide or, preferably, barium sulphate, at a concentration of about 5 to 35% weight or preferably from 13 to 15% weight. Barium sulphate is an inert biocompatible material that will render the fasteners and other components of the coupler radio-opaque for visualization postoperatively if desired.

These fasteners 20, 30 replace a standard anastomotic staple line. Each of these fasteners is plate shaped and contains a central toric section 22, 32 which allow positioning of applier 10 therein. This toric section also allows the pull-through function of the fastener system. Also, at least one of the fasteners 20 has legs or prongs 24 which may be sharpened so as to pierce tissue. Optionally, the prongs may be split along line 24s, to create a spring-like effect. The prongs may be fabricated from the same material as listed for the fasteners 20, 30.

Springs 8 may be added to provide a more uniform controlled compression of the inverted bowel tissue. Helical springs are shown in FIG. 2, but other configurations could be used including but not limited to leaf springs or compressible foam washers. The spring material can be metallic or non-metallic. It is possible to specify a spring constant to achieve a pressure to ensure hemostasis. Experiments conducted on the colon of anesthetized canines, as a model for human colon, would suggest that the springs be selected to achieve a pressure distribution on the ring 39 of at least about 8 to 12 gms/mm$^2$. Too low a pressure may result in leakage and too high a pressure to excessive tissue necrosis.

The other fastener 30 has multiple slots or receivers 34 which correspond to the prongs 24 on fastener 20. This arrangement allows each of the prongs 24 to have little or no difficulty in alignment within the receivers 34 on the other fastener 30. Each fastener 20, 30 generally has at least six such prongs and receivers 24, 34.

The alignment aspect is very important concerning these fasteners 20, 30. It is to be realized that with conventional staples, and conventional staplers, the staples are pre-aligned with anvils so that the staples are readily formed after piercing through tissue. In contrast, it is necessary to have these fasteners 20, 30 self-aligning so that the fasteners themselves meet with one another. Thus, the prongs 24 are configured so that they will readily be urged into each of the receiving receivers 34. The receivers 34 are equal in number to the prongs 24 and are wide enough so that the prongs 24 will fit within each of the receivers 34. Of course, as seen herein, the fasteners 20,30 can each be provided with prongs 24 and receivers 34, which allows more secure compression after emplacement of plates 20, 30. Also, toric sections 22,32 have alignment means comprising a slot and groove arrangement, which lines the prongs 24 with receivers 34.

As further seen in FIG. 2, each of the plates 20,30 has attached to it on an internal section, an additional ring 25,35. Each of these rings 25,35 sits securely on a plate 20,30. Each of the plates 25,35 are provided with tissue adhering pins 29,39. The pins 29,39 are capable of adhering to tissue after suction applied to the coupler mechanism 10 along the compression means 20,30. The pins may be fabricated from metal or, preferably, from a reasonably stiff biocompatible absorbable polymer such as, for example, but not limited to, polyglycolide, or a copolymer of lactide and glycolide. The polymers may contain fillers as described for the fasteners and prongs of the device.

The plates 20, 30 are formed to be generally thin (about 0.010" to 0.030" thick) so that they do not take up much space within the housing of the applier 10 or between tissue. Naturally, such reduced thickness is configured so as to not inhibit holding strength of the fasteners 20, 30. For example, for bowel anastomosis, fasteners 20,30 typically are made in sizes of 10, 18, 21, 25, 29 and 33 mm diameters. These allow for accurate placement for anastomosis through a trocar, like the Endopath TM trocar made by Ethicon, Inc., or to correspond to typical anastomotic instruments. Materials may be used that are initially hard and then terminally soft absorbable polymers, such that their consistency at the time of their expulsion is soft and pliable. These permit usage of such anastomotic rings in other sites, where absorption rather than expulsion is the procedure the body uses to remove these plates.

As seen in FIG. 2, each of the legs 24 has flanges 27, such that a number of useful gap setting distances are provided. The user is able to choose over a relatively infinite range, the appropriate spacing between the two rings plates 20,30 with flanges 25 locked on detents 37 contained in each hole 34. This can be better understood by reference to Ser. No. 709,860, incorporated herein by reference.

The introducer mechanisms 40,50 are generally seen in FIGS. 2, 3 and 4 can be found also in FIG. 2 coupled to the compression plates 20,30. A first introducer mechanism 40 is generally found to be on the proximal side of the anastomosed tissue. A latch 51 attaches plate 20 to introducer portion 40 at notch 41. This introducer portion 40 contains a generally conical shape 42 with a generally cylindrical interior portion 44. It can be seen that there are acceptor holes 46 which are meant to attach to the prongs 24 of one of the compression plates. The generally tubular internal portion 44 is formed with ridges 48 which are able to mate with the opposite distal portion 50. The tubular section 44 contains an interior hollow cross-section into which the applier 10 is able to be placed.

The introducer portion preferably consists of a material that will soften and dissolve or hydrolyze in the bowel in less than about 24 hours so it can be expelled. Generally, this material may be formed from a water soluble material such as, for example, gelatin, albumin, dextran, alginates or chitosan, or preferably from synthetic materials such as, for example, modified celluloses (e.g., hydroxyproply-, hydroxypropylmethyl, carboxymethyl-), the modified thermoplastic starches, polyacrylamides, polyacrylic acids, polyvinylpyrrolidone, polyethylene oxides or polyvinyl alcohols. Most preferable from a blend of polymers is a material which provides good dimensional stability upon short term exposure to moisture, e.g., during the intraoperative time to accomplish the anastomosis, and yet will soften and dissolve within, say, 5 to 76 hours and preferably in about 24 hours and be expelled when exposed to the fluids, particularly water, in the bowel.

A good example of a material that will accomplish this is a polyvinyl alcohol containing a plasticizer to allow the blend to be melted processed, eg. injection molded. A better example is a blend of 5 to 20% weight nylon 6, about 15% plasticizer and the balance of polyvinyl alcohol 88 to 99+% alcoholized. An even better example is a blend of 5 to 10% weight nylon 6, about 15% glycerine as plasticizer and the balance a polyvinyl alcohol about 88% alcoholized. These materials may contain also barium sulphate in the amount described for the other device components, and appropriate stabilizers. Other combinations of water soluble, or hydrolyzable polymers with non-soluble polymers may also come to mind to one skilled in the art.

As further seen in FIG. 2, the distal or opposite introducer portion 50 also contains a conical outer portion. It furthermore contains a tubular inner portion 52. This inner portion contains detents 54 which mate with the slot 45 contained on tubular portion 44 of the proximal portion 40, as can be seen in FIGS. 3 and 4. Thus, both these introducer portions 40,50 are formed in mating relationship. Of course, distal portion 50 also contains receiving holes 76 which are capable of receiving the prongs of the legs 24 contained on an opposite compression member 30 as seen in FIG. 2.

Alternately, as seen in FIG. 2A for instance, a separate latching mechanism 200 is provided. This mechanism mates with tubular portion 44, and its slot 45, on the proximal side of the device at mating section 210. As well, latching mechanism 200 mates with tubular portion 52 and detents 54 on the distal end of the device, at mating section 220. Also, it will be seen that in FIG. 2A, plate 20 is already attached to introducer portion 40. However, pins 29, 39 have been removed from the plates 20, 30, and are placed on rings 120, 130. These rings 120, 130 contain inverted pins 129, 139. It has been found that in certain procedures, latching mechanism 200 and/or inverted pins 129, 139 may be used to facilitate tissue manipulation, to perform the endoscopic anastomosis, and ultimately to enhance healing.

As seen in FIGS. 1, 5, 6, 7, and 8, there is also described an applier for applying both the introducer portions 40,50 and the compression members 20,30 laparoscopically. This applier 10 contains retention pins 12 contained at the distal end of the shaft 14. These pins 12 are actuated by operation of the handle portion 16. The button 17 on the end of handle portion 16 is capable of causing the pins 12 to retract at the opposite end of the shaft 14. Thus, it allows the engagement or disengagement of either introducer member 40 or 50. Of course, each of these introducer members 40 or 50 will have a compression plate 20 or 30 attached to it when attached to the tissue.

As seen in FIGS. 5 and 6, there is further contained a knife blade 19. This knife blade 19 is activated by the operation of handle portion 18, 18'. This knife blade 19 is caused to pierce the tissue captured within the lumen described by any of the introducer portions which also hold a compression member 20 or 30.

Optionally, there are contained in the hollow shaft 12 holes 11 which are capable of causing suction of tissue to either introducer portion 40 or 50 as well as the compression members 20 and 30. Suction is provided along line S to holes 11.

In operation, in FIGS. 5, 6, 7 and 8 the device of this invention is delivered to the abdominal cavity in a two-step process. First, a distal introducer 40 with a compression plate 20 and ring 25 attached is loaded onto the cylindrical applier at the pins 12 so that it is able to be inserted stably within a trocar. After emplacement within a trocar, the introducer and compression member is positioned within a bowel section. Of course, the bowel section must previously be cut. Thereafter, the anastomotic introducer is placed into the bowel, and suction is applied so that the pins 29 of ring 25 are caused to hold tissue thereon. The handle 16 of the applier remains external of the body cavity through the trocar cannula. The combined applier 10 and anastomotic coupling mechanism 50,20 form a generally cylindrical shape which allows the surgeon to position the coupler body half 50,20 within the body colon lumen.

Once within the distal lumen of the sectioned bowel, the surgeon holds the applier handle 16 while working the bowel wall over the pins 29 located about the radius of the compressive ring 25. To assist in the manipulation of the bowel and secure it to the coupler half, the surgeon may apply suction to the connector on the applier handle via the hollow shaft of the applier handle 16 to holes 11 in the body circumference in the body shaft of the introducer applier 10. The surgeon then pushes on the handle 18 to engage a cylindrical knife 19. The cylindrical knife 19 which travels toward the coupler half to both push the bowel to clamp it to the prongs 24 and then to cut the internal portion of the lumen held within the cylinder 11 of applier 10. The next step is to release the bowel and coupler half 50,20 from the applier 10, by pressing button 17 to disengage pins 12 on shaft 14.

Thereafter, the steps are repeated for the proximal or opposite portion of the bowel.

Another form of this invention is that the pins 29, 39 are separate from plates 20, 30 and are fired by the applier to impale the tissue to the plates 20, 30 in a manner similar to a staple, fired into a receiver. This is described above, in conjunction with FIG. 2A.

Figure 9:
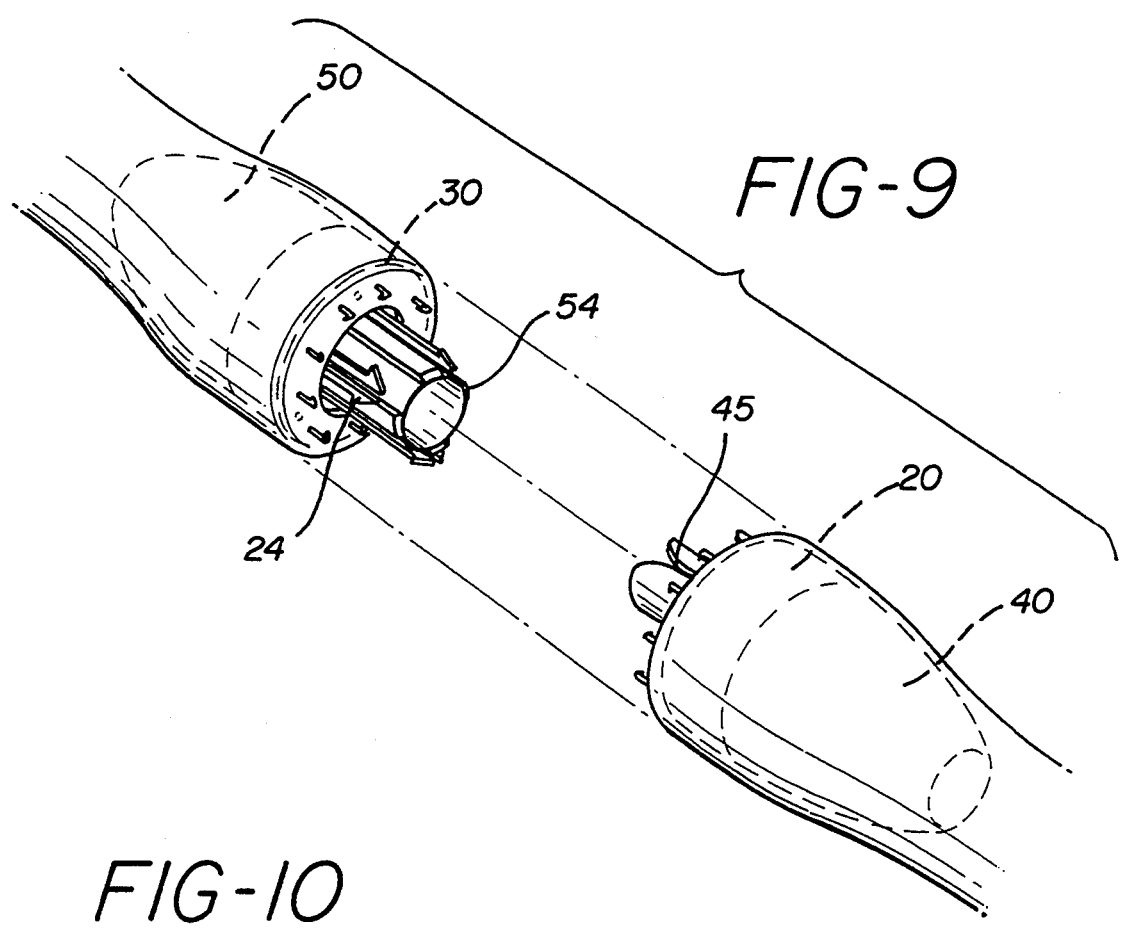
FIGS. 9 and 10 are perspective views of the introducer portions of the anastomotic coupler with compression halves placed therebetween.
Figure 10:
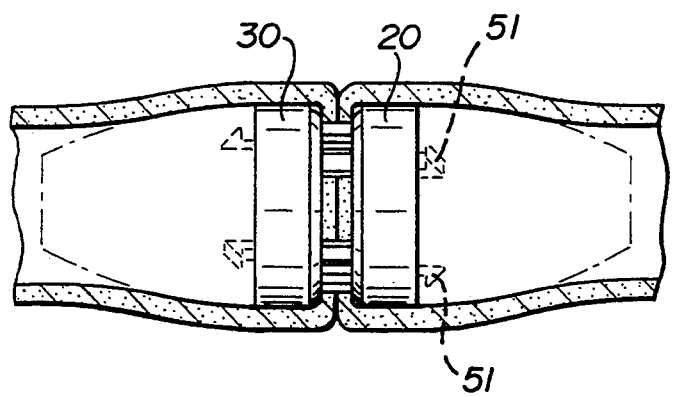
Figure 11:
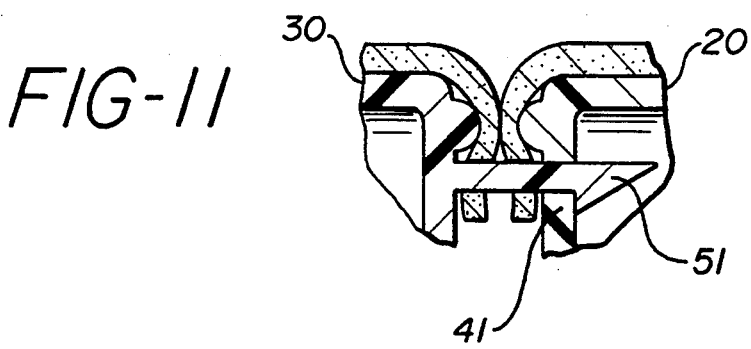
FIG. 11 is a particularized cross-sectional view of the mating halves of FIG. 10.

The uniqueness of the instant invention is seen in FIGS. 9, 10, and 11. Now the proximal and distal sections of the bowel are both fitted to each half of the coupler 40,50, the applier may be withdrawn from a trocar, and the surgeon may grasp each of the halves so that they snap into place. This is accomplished by mating latches 51 with notches 41. There may be ratchets placed on the prongs 24, to enable the surgeon to create the desired compression so that the tissue is properly anastomosed.

Of course, the design of FIG. 2A is attached so that connection is made as in FIGS. 10A and 11A. Indeed, without latching mechanism 200, but using rings 120, 130, latching may be accomplished as in FIG. 11B.

The desired compression could also be accomplished in a number of other methods including the use of metallic springs, non-metallic springs, compression foams, or even a fixed gap selected externally and gauged according to the tissue thickness.

Thus, this coupling device accomplishes some very unique features. First, there is compression at the serosa junction in steps of between 0.5 mm to 2 mm to accommodate various bowel tissue thicknesses. Second, there are pins which hold and stabilize the lumenal tissue sections during healing. Third, optimally, there is a two-step biodegradation, first in about 24 hours for the introducer portions 40,50 and then about 2 to 3 weeks for the compression portions 20, 30. Fourth, the applier 10 is able to bring the device into the surgical field via a trocar. It operates as a stable work platform and manipulator and contains an "integrated anvil and cutter" for assisting in affixing the luminal walls to the pins 29 for removal of the excess inverted tissue portion. Fifth, the instrument 10 also contains suction mechanism via the hollow shaft 12 to aid in tissue manipulation, and device placement.

Yet, what is clearly unique is that there is no purse string suturing of the bowel required so that this mechanism may easily be operated for laparoscopic application. It allows surgeon's skill levels to be lowered because there is less skillful steps to be performed in accomplishing anastomosis. The mechanism resides fully within the bowel so that it is easily removed, and takes the shape similar to a bowel dilator which aids in insertion and expansion of the bowel lumen. Because there are openings in the introducers 40,50 and the compression plates 20,30, and the introducers 40,50 are dissolved soon after the endoscopic procedure, there is easy passage of gas and excrement during healing. This, it is believed will improve healing time, and, of course, patient comfort.

These and other embodiments of the invention have been described as above. Of course, it may be possible to vary the applier and fastener of the present invention without deviating from the intent of this invention. For instance, it is possible to create an apparatus with a curved longitudinal shaft, or having a flexible shaft, or where the shaft portion near the distal end contains a trocar mechanism for piercing tissue. What is to be realized is that it is the following claims and their equivalents which are meant to cover the scope of the invention.

What is claimed is:

1. In combination: an anastomotic coupler mechanism having a hollow tubular interior and
   an applier comprising a tubular shaft with proximal and distal ends and defining an axis for placement within said hollow interior;
   a retaining mechanism at said distal end having a first position for holding said shaft within said hollow tubular interior; and
   an activating mechanism located at said shaft proximal end, capable of activating said retaining mechanism to cause said retaining mechanism to move from its first position to a second position wherein said coupler may be released from said shaft; and wherein said activating mechanism is a push button means which is connected to said retaining mechanism, and said push button means capable of causing said retaining mechanism to move from said first position transverse to said shaft to said second position.

2. The applier of claim 1 wherein said retaining mechanism comprises a pair of friction members capable of movement in a direction transverse to said shaft.

3. The applier of claim 1 wherein said retaining mechanism is capable of holding said hollow interior of said coupler in a friction fit.

4. The applier of claim 1 wherein said shaft is hollow and contains openings at both said proximal and distal ends wherein suction may be applied to said shaft.

5. The applier of claim 1 further comprising knife means at said distal end, said knife means activated by said activating mechanism so that said knife means moves along said shaft axis.

6. The applier of claim 5 wherein said knife means is activated to move distally along said shaft.

7. In combination: an anastomotic coupling mechanism having a hollow tubular interior and
   an applier comprising a tubular shaft with proximal and distal ends and defining an axis for placement within said hollow interior;
   a retaining mechanism at said distal end comprising a pair of frictional members initially in a first position protruding from said shaft to engage said coupling mechanism, and moveable in a direction transverse to said shaft to a second position wherein said frictional members no longer engage said coupling mechanism; and
   activating means located at said shaft proximal end, and capable of activating said retaining means to move from said first position to said second position; and wherein said activating means is a push button means which is connected to said retaining mechanism, and said push button means capable of causing said retaining mechanism to move from said first position transverse to said shaft to said second position.

8. The applier of claim 7 wherein said shaft is hollow and contains openings at both said proximal and distal ends.

9. The applier of claim 7 further comprising knife means at said distal end, said knife means activated by said activating means so that said knife means moves along said shaft axis.

10. The applier of claim 9 wherein said knife means is activated to move distally along said shaft.

11. An anastomotic coupler introducer mechanism comprising:
    a pair of longitudinally arranged generally conical disintegrable introducer halves having a central longitudinal axis and said conical shape having a longitudinal length greater than the radial length from said longitudinal axis transverse to said longitudinal length, each said half containing a hollow cylindrical interior portion;
    a first of said interior portions having detent means for engaging the opposite of said interior portions; and
    the second of said interior portions contains a tubular channel to insert within the hollow cylindrical interior portion of said first interior portion for engagement with the first interior portion.

12. The mechanism of claim 1 wherein the outer diameter of said introducer halves is between 10 mm and 33 mm.

13. The mechanism of claim 11 wherein said detent means in a first of said introducer halves comprises a plurality of latches for engaging said second of said introducer halves.

14. The mechanism of claim 13 wherein said latches have a longitudinal split section.

15. An anastomotic coupler mechanism comprising:
    a pair of generally conical introducer halves, each said half containing a hollow cylindrical interior portion and having a base opposite a base contained on the other half; and
    each of said introducer halves associated with a circular tissue engaging ring at its base, said ring comprising a plurality of piercing pins and a plurality of receiving spaces, the number of pins on one ring corresponding to the number of spaces on the opposite ring.

16. The mechanism of claim 15 wherein at least one of said introducer halves contains a circular base, and said spaces in said at least one introducer half comprising a plurality of receiving holes at its circumference.

17. The mechanism of claim 16 wherein the opposite of said introducer halves contains a circular base, said introducer half containing a plurality of flanges at its circumference corresponding to said receiving holes.

18. An anastomotic coupler mechanism comprising:
    a pair of generally conical introducer halves, each said half containing a hollow cylindrical interior portion; and
    each of said introducer halves containing a circular tissue engaging ring at its base, comprising a plurality of piercing pins and a plurality of receiving spaces, the number of pins on one half corresponding to the number of spaces on the opposite half and further comprising:
    wherein a first of said interior portions has a ring detent means for engaging the opposite of the introducer portions; and
    wherein the interior portion opposite from said first interior portion contains a ring with a tubular channel to insert within the hollow cylindrical interior portion of said first interior portion for engagement with the first of said interior portion.

19. The mechanism of claim 18 wherein said introducer halves are disintegrable.

20. The mechanism of claim 18 wherein said second interior portion contains a plurality of slots, for locking to said detent means.

21. The mechanism of claim 18 wherein the outer diameter of said introducer halves is between 10 mm and 33 mm.

22. An anastomotic coupler mechanism comprising:
a pair of generally conical introducer halves, each said half containing a hollow cylindrical interior portion; and
each of said introducer halves containing a circular tissue engaging ring at its base, comprising a plurality of piercing pins and a plurality of receiving spaces, the number of pins on one half corresponding to the number of spaces on the opposite half wherein said introducer halves are disintegrable and further wherein said introducer halves are formed from a different disintegrable material than said rings.

23. The mechanism of claim 22 wherein said introducer halves are formed from a material capable of disintegrating within 24 hours.

24. The mechanism of claim 23 wherein said introducer halves are formed from a blend of non water soluble and water soluble polymer.

25. The mechanism of claim 24 wherein said introducer halves are formed from a thermoplastic blend of a nylon 6, of up to 10% weight, 10 to 15% of a plasticizer and the balance a polyvinyl alcohol 88 to 99+% alcoholized.

26. The combination of claim 22 wherein said rings are formed from a blend of lactide-rich, lactide, glycolide copolymer and a glycolide rich, lactide, glycolide co-polymers.

27. The combination of claim 22 wherein said rings are formed from a blend of two polymers, one being a lactide-rich, lactide, glycolide copolymer and the other a polymer of substantially polydioxanone.

28. An anastomotic coupler introducer mechanism comprising:
a pair of generally conical disintegrable introducer halves, each said half containing a hollow cylindrical interior portion;
a first of said interior portions having detent means for engaging the opposite of said interior portions; and
the second of said interior portions contains a tubular channel to insert within the hollow cylindrical interior portion of said first interior portion for engagement with the first interior portion; and further containing a plurality of impaling prongs associated with at least one of said introducer halves.

29. The mechanism of claim 28 wherein said impaling prongs are contained in a ring.

30. The mechanism of claim 29 wherein said prongs on said ring to face an introducer half.

* * * * *